US011225684B2

(12) United States Patent
Bres et al.

(10) Patent No.: US 11,225,684 B2
(45) Date of Patent: Jan. 18, 2022

(54) METHOD AND DEVICE FOR SNP GENOTYPING

(71) Applicant: ETABLISSEMENT FRANCAIS DU SANG, La Plaine Saint Denis (FR)

(72) Inventors: Jean-Charles Bres, Vacquieres (FR); Julien Gomez-Martinez, Juvignac (FR)

(73) Assignee: ETABLISSEMENT FRANCAIS DU SANG, La Plaine Saint Denis (FR)

( * ) Notice: Subject to any disclaimer, the term of this patent is extended or adjusted under 35 U.S.C. 154(b) by 87 days.

(21) Appl. No.: 15/758,734

(22) PCT Filed: Sep. 9, 2016

(86) PCT No.: PCT/FR2016/052272
§ 371 (c)(1),
(2) Date: Mar. 9, 2018

(87) PCT Pub. No.: WO2017/042509
PCT Pub. Date: Mar. 16, 2017

(65) Prior Publication Data
US 2018/0258475 A1 Sep. 13, 2018

(30) Foreign Application Priority Data
Sep. 11, 2015 (FR) ...................... 1558465

(51) Int. Cl.
*C12Q 1/6827* (2018.01)
*C12Q 1/6881* (2018.01)
(52) U.S. Cl.
CPC ......... *C12Q 1/6827* (2013.01); *C12Q 1/6881* (2013.01); *C12Q 2600/156* (2013.01); *C12Q 2600/16* (2013.01)
(58) Field of Classification Search
CPC ............ C12Q 1/6827; C12Q 2531/107; C12Q 2537/143; C12Q 2565/625; C12Q 1/6881; C12Q 2600/156; C12Q 2600/16
See application file for complete search history.

(56) References Cited

U.S. PATENT DOCUMENTS

| 10,000,788 B2 * | 6/2018 | Straus ................ G01N 21/6428 |
| 2005/0227275 A1 * | 10/2005 | Jung .................... C12Q 1/6816 435/6.16 |
| 2010/0029496 A1 * | 2/2010 | Cary ...................... C12Q 1/689 506/9 |
| 2012/0035060 A1 | 2/2012 | Lin et al. | |

FOREIGN PATENT DOCUMENTS

| EP | 2 278 334 | 1/2011 |
| WO | WO 2012/040403 | 3/2012 |
| WO | WO 2013/122453 | 8/2013 |

OTHER PUBLICATIONS

Moers et al., Antimicrobial Agents and Chemotherapy, vol. 59, No. 1, pp. 365-371, Nov. 3, 2014.*
Sabastian et al., Clinica Chimica Acta, vol. 429, pp. 198-205, Dec. 17, 2013.*
Ang, G. Y. et al. "Ambient temperature detection of PCR amplicons with a novel sequence-specific nucleic acid lateral flow biosensor" *Biosensors and Bioelectronics*, May 15, 2012, pp. 151-156, vol. 38, No. 1.
Elenis, D. S. et al. "A nanoparticle-based sensor for visual detection of multiple mutations" *Nanotechnology*, Mar. 10, 2011, pp. 1-9, vol. 22, No. 15.
Mens, P. F. et al. "Direct Blood PCR in Combination with Nucleic Acid Lateral Flow Immunoassay for Detection of *Plasmodium* Species in Settings Where Malaria Is Endemic" *Journal of Clinical Microbiology*, Nov. 2012, pp. 3520-3525, vol. 50, No. 11.
Ngom, B. et al. "Development and application of lateral flow test strip technology for detection of infectious agents and chemical contaminants: a review" *Analytical and Bioanalytical Chemistry*, Apr. 27, 2010, pp. 1113-1135, vol. 397, No. 3.
Sebastian, T. et al. "Integrated amplification microarray system in a lateral flow cell for warfarin genotyping from saliva" *Clinica Chimica Acta*, 2014, pp. 198-205, vol. 429.
Song, K.-S. et al. "A new platform for a convenient genotyping system" *Chemical Communications*, 2013, pp. 2661-2663, vol. 49, No. 26.
Song, K.-S. et al. "MTB-DR-RIF 9G test: Detection and discrimination of tuberculosis and multi-drug resistant tuberculosis strains" *Tuberculosis*, Sep. 5, 2015, pp. 780-785, vol. 95, No. 6; Online Supporting Information, pp. 1-5.
Lee, S. H. et al. "Rapid ABO Genotyping Using Whole Blood without DNA Purification" *Korean Journal of Laboratory Medicine*, Jun. 30, 2009, pp. 231-237, vol. 29, No. 3.
Xu, Y. et al. "Fluorescent Probe-Based Lateral Flow Assay for Multiplex Nucleic Acid Detection" *Analytical Chemistry*, Jun. 3, 2014, pp. 5611-5614, vol. 86, No. 12; Supplementary information, pp. S1-S9.
Written Opinion in International Application No. PCT/FR2016/052272, dated Nov. 22, 2016, pp. 1-10.
Cooney, C. G. et al. "A plastic, disposable microfluidic flow cell for coupled on-chip PCR and microarray detection of infectious agents" *Biomed Microdevices*, 2012, pp. 45-53, vol. 14.

* cited by examiner

*Primary Examiner* — Cynthia B Wilder
(74) *Attorney, Agent, or Firm* — Saliwanchik, Lloyd & Eisenschenk

(57) ABSTRACT

The present invention relates to a method for genotyping single nucleotide polymorphisms (SNPs) using a lateral flow test device. The invention also relates to a kit comprising said lateral flow test device and also to the use thereof for genotyping single nucleotide polymorphisms (SNPs).

19 Claims, 6 Drawing Sheets

Specification includes a Sequence Listing.

|  |  | Phenotypes |
|---|---|---|
|  |  | FY system |
| Sample #1 | Serological technique | FY: 1,2 |
|  | Reference genotyping technique | FY: 1,2 (*FY*1/*2*) |
|  | Migration on nitrocellulose membrane technique | FY: 1,2 (*FY*1/*2*) |
| Sample #2 | Serological technique | FY: 1,2 |
|  | Reference genotyping technique | FY: 1,2 (*FY*1/*2*) |
|  | Migration on nitrocellulose membrane technique | FY: 1,2 (*FY*1/*2*) |
| Sample #3 | Serological technique | FY: 1,-2 |
|  | Reference genotyping technique | FY: 1,-2 (*FY*1/*1*) |
|  | Migration on nitrocellulose membrane technique | FY: 1,-2 (*FY*1/*1*) |
| Sample #4 | Serological technique | FY: 1,-2 |
|  | Reference genotyping technique | FY: 1,-2 (*FY*1/*1*) |
|  | Migration on nitrocellulose membrane technique | FY: 1,-2 (*FY*1/*1*) |
| Sample #5 | Serological technique | FY: -1,2 |
|  | Reference genotyping technique | FY: -1,2 (*FY*2/*2*) |
|  | Migration on nitrocellulose membrane technique | FY: -1,2 (*FY*2/*2*) |
| Sample #6 | Serological technique | FY: -1,2 |
|  | Reference genotyping technique | FY: -1,2 (*FY*2/*2*) |
|  | Migration on nitrocellulose membrane technique | FY: -1,2 (*FY*2/*2*) |

Figure 2

|  |  | Phenotypes |
|---|---|---|
|  |  | JK system |
| Sample #7 | Serological technique | JK: 1, 2 |
|  | Reference genotyping technique | JK: 1, 2 (*JK*1/*2*) |
|  | Migration of amplified targets on nitrocellulose membrane technique | JK: 1, 2 (*JK*1/*2*) |
| Sample #8 | Serological technique | JK: 1, 2 |
|  | Reference genotyping technique | JK: 1, 2 (*JK*1/*2*) |
|  | Migration of amplified targets on nitrocellulose membrane technique | JK: 1, 2 (*JK*1/*2*) |
| Sample #9 | Serological technique | JK: 1, -2 |
|  | Reference genotyping technique | JK: 1, -2 (*JK*1/*1*) |
|  | Migration of amplified targets on nitrocellulose membrane technique | JK: 1, -2 (*JK*1/*1*) |
| Sample #10 | Serological technique | JK: 1, -2 |
|  | Reference genotyping technique | JK: 1, -2 (*JK*1/*1*) |
|  | Migration of amplified targets on nitrocellulose membrane technique | JK: 1, -2 (*JK*1/*1*) |
| Sample #11 | Serological technique | JK: -1, 2 |
|  | Reference genotyping technique | JK: -1, 2 (*JK*2/*2*) |
|  | Migration of amplified targets on nitrocellulose membrane technique | JK: -1, 2 (*JK*2/*2*) |
| Sample #12 | Serological technique | JK: -1, 2 |
|  | Reference genotyping technique | JK: -1, 2 (*JK*2/*2*) |
|  | Migration of amplified targets on nitrocellulose membrane technique | JK: -1, 2 (*JK*2/*2*) |

Figure 3

|  |  | Phenotypes | | |
| --- | --- | --- | --- | --- |
|  |  | JK | FY | MNS |
| Sample #13 | Serological technique | JK: 1, -2 | FY: -1,2 | MNS: 3, -4 |
| | Reference genotyping technique | JK: 1, -2 (*JK*1/*1*) | FY: -1,2 (*FY*2/*2*) | MNS: 3, -4 (*MNS*3/*3*) |
| | Migration on nitrocellulose membrane technique | JK: 1, -2 (*JK*1/*1*) | FY: -1,2 (*FY*2/*2*) | MNS: 3, -4 (*MNS*3/*3*) |
| Sample #14 | Serological technique | JK: 1, 2 | FY: 1,2 | MNS: -3, 4 |
| | Reference genotyping technique | JK: 1, 2 (*JK*1/*2*) | FY: 1,2 (*FY*1/*2*) | MNS: -3, 4 (*MNS*4/*4*) |
| | Migration on nitrocellulose membrane technique | JK: 1, 2 (*JK*1/*2*) | FY: 1,2 (*FY*1/*2*) | MNS: -3, 4 (*MNS*4/*4*) |
| Sample #15 | Serological technique | JK: -1, 2 | FY: 1,2 | MNS: 3, 4 |
| | Reference genotyping technique | JK: -1, 2 (*JK*2/*2*) | FY: 1,2 (*FY*1/*2*) | MNS: 3, 4 (*MNS*3/*4*) |
| | Migration on nitrocellulose membrane technique | JK: -1, 2 (*JK*2/*2*) | FY: 1,2 (*FY*1/*2*) | MNS: 3, 4 (*MNS*3/*4*) |
| Sample #16 | Serological technique | JK: -1, 2 | FY: 1,-2 | MNS: 3, 4 |
| | Reference genotyping technique | JK: -1, 2 (*JK*2/*2*) | FY: 1,-2 (*FY*1/*1*) | MNS: 3, 4 (*MNS*3/*4*) |
| | Migration of amplified targets on nitrocellulose membrane technique | JK: -1, 2 (*JK*2/*2*) | FY: 1,-2 (*FY*1/*1*) | MNS: 3, 4 (*MNS*3/*4*) |
| Sample #17 | Serological technique | JK: 1, 2 | FY: -1,2 | MNS: 3, -4 |
| | Reference genotyping technique | JK: 1, 2 (*JK*1/*2*) | FY: -1,2 (*FY*2/*Fy*) | MNS: 3, -4 (*MNS*3/*3*) |
| | Migration of amplified targets on nitrocellulose membrane technique | JK: 1, 2 (*JK*1/*2*) | FY: -1,2 (*FY*2/*Fy*) | MNS: 3, -4 (*MNS*3/*3*) |

Figure 4

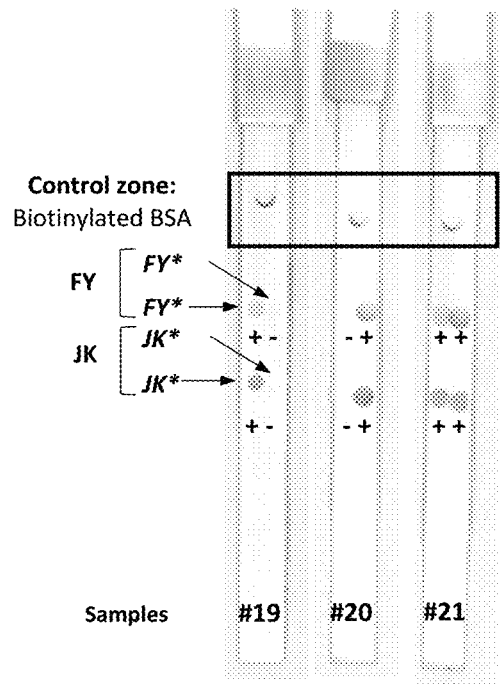

Figure 5

|  |  | Phenotypes | |
| --- | --- | --- | --- |
|  |  | JK | FY |
| Sample #19 | Serological technique | JK: 1, -2 | FY: 1,-2 |
| | Reference genotyping technique | JK: 1, -2 (JK*1/*1) | FY: 1,-2 (FY*1/*1) |
| | Migration on nitrocellulose membrane technique | JK: 1, -2 (JK*1/*1) | FY: 1,-2 (FY*1/*1) |
| Sample #20 | Serological technique | JK: -1, 2 | FY: -1,2 |
| | Reference genotyping technique | JK: -1, 2 (JK*2/*2) | FY: -1,2 (FY*2/*2) |
| | Migration on nitrocellulose membrane technique | JK: -1, 2 (JK*2/*2) | FY: -1,2 (FY*2/*2) |
| Sample #21 | Serological technique | JK: 1, 2 | FY: 1,2 |
| | Reference genotyping technique | JK: 1, 2 (JK*1/*2) | FY: 1,2 (FY*1/*2) |
| | Migration on nitrocellulose membrane technique | JK: 1, 2 (JK*1/*2) | FY: 1,2 (FY*1/*2) |

Figure 6

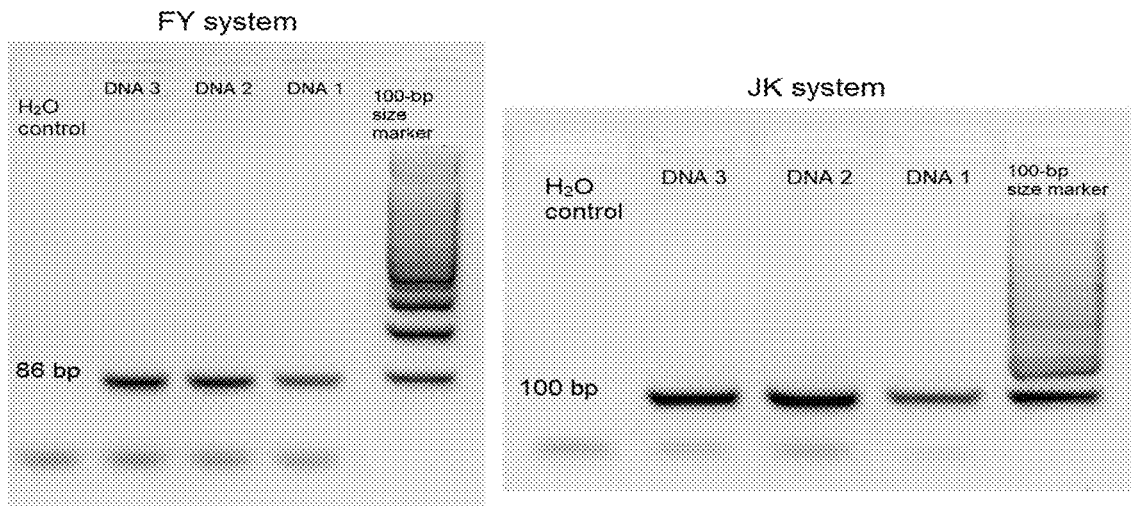

Figure 7

|  |  | Phenotypes | | |
| --- | --- | --- | --- | --- |
|  |  | JK | FY | MNS |
| Sample #22 | Serological technique | JK: 1, 2 | FY: -1,2 | MNS: 3, -4 |
|  | Reference genotyping technique | JK: 1, 2 (JK*1/*2) | FY: -1,2 (FY*2/*Fy) | MNS: 3, -4 (MNS*3/*3) |
|  | Migration on nitrocellulose membrane technique | JK: 1, 2 (JK*1/*2) | FY: -1,2 (FY*2/*Fy) | MNS: 3, -4 (MNS*3/*3) |
| Sample #23 | Serological technique | JK: 1, -2 | FY: -1, -2 or FYnull | MNS: -3, 4 |
|  | Reference genotyping technique | JK: 1, -2 (JK*1/*1) | FY: -1, -2 (FY*Fy/*Fy) | MNS: -3, 4 (MNS*4/*4) |
|  | Migration on nitrocellulose membrane technique | JK: 1, -2 (JK*1/*1) | FY: -1, -2 (FY*Fy/*Fy) | MNS: -3, 4 (MNS*4/*4) |
| Sample #24 | Serological technique | JK: 1, -2 | FY: 1,-2 | MNS: -3, 4 |
|  | Reference genotyping technique | JK: 1, -2 (JK*1/*1) | FY: 1,-2 (FY*1/*Fy) | MNS: -3, 4 (MNS*4/*4) |
|  | Migration on nitrocellulose membrane technique | JK: 1, -2 (JK*1/*1) | FY: 1,-2 (FY*1/*Fy) | MNS: -3, 4 (MNS*4/*4) |
| Sample #25 | Serological technique | JK: -1, 2 | FY: -1,2 | MNS: 3, 4 |
|  | Reference genotyping technique | JK: -1, 2 (JK*2/*2) | FY: -1,2 (FY*2/*2) | MNS: 3, 4 (MNS*3/*4) |
|  | Migration on nitrocellulose membrane technique | JK: -1, 2 (JK*2/*2) | FY: -1,2 (FY*2/*2) | MNS: 3, 4 (MNS*3/*4) |

Figure 8

METHOD AND DEVICE FOR SNP GENOTYPING

CROSS-REFERENCE TO RELATED APPLICATION

This application is the U.S. national stage application of International Patent Application No. PCT/FR2016/052272, filed Sep. 9, 2016.

The Sequence Listing for this application is labeled "Seq-List.txt" which was created on Feb. 26, 2018, and is 6 KB. The entire content of the sequence listing is incorporated herein by reference in its entirety.

The present invention relates to a new method for single-nucleotide polymorphism (SNP) genotyping.

BACKGROUND OF THE INVENTION

A single-nucleotide polymorphism (SNP) is a variation in a single base-pair in the genome between individuals of the same species or between chromosomes of the same pair. SNPs make up 90% of all human genetic variations. They are found about every 1000 bases in the human genome and to date more than 1.8 million SNPs are listed and available in specialized databases. Utilization of these databases has shown that these SNPs can be used not only for purposes of forensic medicine to distinguish individuals but also to diagnose or determine predispositions for certain diseases, to predict the gravity of the condition or the patient's response to a treatment, or to determine an individual's blood group.

There are many methods for detecting SNPs, such as DNA microarrays, allele-specific oligonucleotide (ASO) hybridization, DNA sequencing, single-strand conformation polymorphism (SSCP) analysis, mass spectrometry, primer extension, restriction fragment length polymorphism analysis, and allele-specific oligonucleotide ligation. However, most of these techniques are expensive, complex to set up and do not enable one-off analyses with easy-to-use processes.

In recent years, new simplified techniques have thus been developed in which SNPs are detected using simple dipstick tests (or lateral-flow assays) which allow the result to be obtained by visual inspection (Litos et al., 2009; Sapountzi et al., 2015). These new techniques are essentially based on PCR amplification of the target DNA using primers specific for the allele of interest. This means that the amplification reaction takes place only if the 3' region of the primer is perfectly complementary to the target sequence. Each specific primer for an allele thus comprises a sequence adjacent to the SNP site with a 3' nucleotide complementary to the allelic variant, a spacer arm and a 5' label allowing it to hybridize with the probes immobilized on the dipstick. Litos et al. propose a technique in which several SNPs can be genotyped simultaneously on the same dipstick. To that end, each specific primer for an allele comprises a different 5' label which will specifically hybridize with one of the probes immobilized on the dipstick. However, despite the progress that has been made, these techniques remain complex to implement, notably because of the use of two successive amplification techniques (PCR then primer-extension reaction) and/or the production of microspheres conjugated to the specific sequences for each allele to be detected and the deposit of these microspheres onto nitrocellulose membranes.

SUMMARY OF THE INVENTION

The inventors have now shown that it was possible to discriminate the different allelic variants of the same SNP from a single amplification product using a lateral-flow assay device.

Thus, according to a first aspect, the present invention concerns an in vitro method for genotyping one or more single-nucleotide polymorphisms (SNPs) in a nucleic acid sample, said method comprising:

a) amplifying one or more regions of the nucleic acid containing the SNP(s) to be genotyped, the amplification products comprising a label capable of directly or indirectly generating a detectable signal, and b) analysing the amplification products obtained in step (a) using a lateral-flow assay device comprising a reaction zone, preferably made of nitrocellulose, comprising one or more nucleotide probes, preferably at least two nucleotide probes, immobilized on distinct sites, each probe having a sequence complementary to an allelic variant of a SNP to be genotyped, the detection of a signal at the probe immobilization site indicating that the nucleic acid comprises the specific allelic variant of the probe.

The amplification is preferably carried out by asymmetric PCR, and more particularly preferably by LATE-PCR.

The simultaneous amplification of several regions of the nucleic acid can be carried out by multiplex PCR.

The amplification products can be 5'-labelled, preferably by the use of 5'-labelled primers during the amplification.

The amplification products can be labelled with a colored, luminescent, fluorescent, phosphorescent or radioactive compound, with an enzyme or the first member of a ligand/anti-ligand pair, preferably with a biotin.

Preferably, the detectable signal is a colored signal visible to the naked eye and the detection is done by simple visual inspection. Preferably, the signal is obtained via the use of a colored particle such as a colloidal gold particle.

Preferably, the lateral-flow assay device used during the method according to the invention comprises a porous matrix comprising (i) a migration buffer application zone, (ii) an amplification product application zone positioned downstream of the migration buffer application zone, and (iii) the reaction zone positioned downstream of the amplification product application zone, and (iv) optionally, a reagent migration monitoring zone downstream of the reaction zone, and/or (v) optionally, a labelling zone comprising a substrate or binding partner specific for the amplification product label capable of directly or indirectly generating a detectable signal, positioned downstream of the migration buffer application zone and upstream of the amplification product application zone, and/or (vi) optionally, an absorbent pad positioned downstream of the reaction zone or the monitoring zone when the latter is present, the various zones of the porous matrix being in fluid communication with the adjacent zone(s) and the absorbent pad being in fluid communication with the porous matrix.

The amplification products can be analysed directly using the lateral-flow assay device with no preliminary purification or denaturation step.

Analysis of the amplification products typically comprises (i) loading the amplification products obtained in step (a) onto the lateral-flow assay device, (ii) applying a migration buffer on said device, (iii) incubating the device until the signals generated directly or indirectly by the amplification product label are detected in the reaction zone and/or a signal is detected in the migration monitoring zone, when the latter is present, and (iv) reading and interpreting the results.

The matrix of the lateral-flow assay device can be made of nitrocellulose, polyester, glass fiber, cellulose fiber, polyether sulphone (PES) and/or cellulose ester. Preferably, the matrix is or comprises a nitrocellulose membrane.

Preferably, the reaction zone of the matrix is made of nitrocellulose. Particularly preferably, the amplification product application zone and/or the monitoring zone of the matrix, preferably the amplification product application zone and the monitoring zone of the matrix, are also made of nitrocellulose. This means that according to certain embodiments, the matrix comprises a nitrocellulose membrane which comprises the amplification product application zone, the reaction zone and the monitoring zone of the matrix. Alternatively, the reaction zone and the monitoring zone of the matrix can be made of nitrocellulose, and the amplification product application zone made of cellulose fiber.

The migration buffer application zone of the matrix and/or the absorbent pad are preferably made of cellulose fiber, and the labelling zone of the matrix is preferably made of glass fiber.

The migration buffer preferably comprises a buffer system for maintaining a neutral pH, one or more surfactants and/or one or more denaturing agents that destabilize hydrogen bonds and non-specific interactions.

The nucleic acid to be genotyped and contained in the sample is preferably genomic DNA, and more particularly preferably, human genomic DNA.

The nucleic acid sample can in particular be a total blood, serum or plasma sample. In this case, the step of amplifying one or more regions of the nucleic acid containing the SNP(s) to be genotyped can be carried out on the total blood, serum or plasma sample, with no preliminary step of partial or total purification of the nucleic acid.

According to a preferred embodiment, the amplification product label is biotin, and the migration buffer or the labelling zone comprises an anti-biotin antibody coupled to a detectable label, preferably coupled to a gold particle.

According to a second aspect, the present invention also concerns a kit comprising a lateral-flow assay device as defined above, and at least one primer pair for amplifying a genomic region containing a SNP. Optionally, the kit can also comprise a migration buffer, the amplification reagents, preferably dNTPs, a polymerase and/or a buffer, and/or an instruction leaflet explaining the use of said kit.

According to a preferred embodiment, the kit comprises one or more primer pairs for amplifying one or more genomic regions containing one or more SNPs associated with blood group antigen systems, preferably the Duffy, MNS and/or Kidd systems. In particular, the kit can comprise one or more primers selected from the group consisting of SEQ ID NO: 1 to 8, and more particularly one or more of the primer pairs (1) SEQ ID NO: 1 and 2, (2) SEQ ID NO: 3 and 4, (3) SEQ ID NO: 5 and 6, and (4) SEQ ID NO: 7 and 8.

The present invention further concerns the use of the kit according to the invention for genotyping one or more SNPs, preferably one or more SNPs associated with blood group antigen systems, according to the method of the invention.

BRIEF DESCRIPTION OF THE DRAWINGS

FIG. 2: List of the phenotypes obtained for the FY system by serological technique (reference technique) and of the phenotypes predicted from the genotypes obtained by the two genotyping methods: (i) DNA microarray (reference genotyping technique) and (ii) by migration on a nitrocellulose membrane according to the method of the present invention, for samples #1 to #6 of FIG. 1A.

FIG. 3: List of the phenotypes obtained for the JK system by serological technique (reference technique) and of the phenotypes predicted from the genotypes obtained by the two genotyping methods: (i) DNA microarray (reference genotyping technique) and (ii) by migration on a nitrocellulose membrane according to the method of the present invention, for samples #7 to #12 of FIG. 1B.

FIG. 4: List of the phenotypes obtained for the JK, FY and MNS systems by serological technique (reference technique) and of the phenotypes predicted from the genotypes obtained by the two genotyping methods: (i) DNA microarray (reference genotyping technique) and (ii) by migration on a nitrocellulose membrane according to the method of the present invention, for samples #13 to #17 of FIGS. 1C and 1D.

FIG. 5: Genotyping results obtained after the migration at 30° C. of biotinylated targets amplified by the duplex LATE-PCR protocol for the JK and FY systems, from genomic DNA samples having different genotypes, on a nitrocellulose membrane (samples #19, #20 and #21).

FIG. 6: List of the phenotypes obtained for the JK and FY systems by serological technique (reference technique) and of the phenotypes predicted from the genotypes obtained by the two genotyping methods: (i) DNA microarray (reference genotyping technique) and (ii) by migration on a nitrocellulose membrane according to the method of the present invention, for samples #19 to #21 of FIG. 5.

FIG. 7: Verification on 2% agarose gel of the products amplified by monoplex LATE-PCR for the JK and FY systems.

FIG. 8: List of the phenotypes obtained for the JK, FY and MNS systems by serological technique (reference technique) and of the phenotypes predicted from the genotypes obtained by the two genotyping methods: (i) DNA microarray (reference genotyping technique) and (ii) by migration on a nitrocellulose membrane according to the method of the present invention, for samples #22 to #25.

DETAILED DESCRIPTION OF THE INVENTION

Figure 1A:
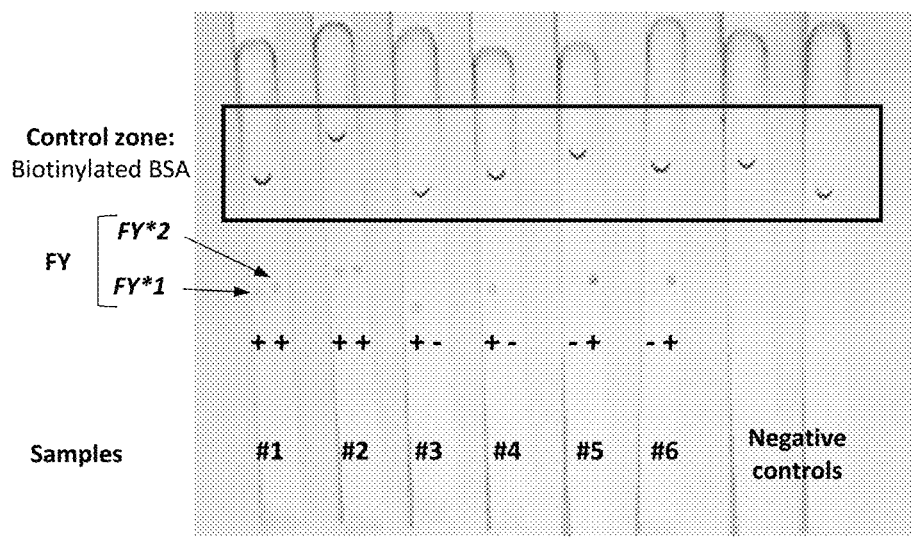
FIG. 1: Genotyping results obtained after the migration of biotinylated targets amplified by monoplex and multiplex LATE-PCR protocols, from genomic DNA samples having different genotypes, on a nitrocellulose membrane. Results obtained after the amplification of samples from various LATE-PCR protocols: (i) monoplex for the (A) FY (samples #1 to #6) and (B) JK (samples #7 to #12) blood group systems, and (ii) multiplex (C) (samples #13, #14 and #15) and (D) (samples #16 and #17). The − and + signs refer to the absence and the presence of the allele, respectively.

Blood grouping is critically important for evaluating the compatibility between the blood of a donor and a recipient during transfusion and for limiting the risks of transfusion reaction or alloimmunization. To date, 35 blood group systems containing more than 300 blood group antigens have been identified. According to current practice, the routine typing of blood bags concerns only a small number of blood group antigens, such as the antigens of the ABO, RH and Kell (KEL) systems. However, other antigens, notably those of the Duffy (FY), MNS (MNS) or Kidd (JK) systems, prove to have clinical significance owing to the frequency of the transfusion reactions caused by the corresponding antibodies.

Although effective for the antigens of the ABO, RH and Kell systems, the extensive typing of blood units by means of conventional serological techniques has several disadvantages. Indeed, these are expensive, single-parameter tests, one of the limiting factors of which is the difficulty of obtaining effective monoclonal antibodies for the various systems. Moreover, in certain clinical situations, such as for immunized or chronically transfused patients, the conventional agglutination techniques cannot be used, thus complicating transfusion management.

Thanks to a better understanding of the molecular basis of blood antigens, it is now possible to determine the blood group of an individual or a blood bag by identifying SNPs in genomic DNA. By way of example, the Kidd system comprises the JK1 and JK2 antigen pair derived from the 838G>A SNP, which generates the co-dominant alleles JK*1 and JK*2 encoding aspartic acid and asparagine residues, respectively, at position 280 of the Kidd glycoprotein.

The inventors have herein developed a simple, rapid and inexpensive technique for determining the blood group phenotype of an individual or a blood sample by genotyping the SNPs associated with various blood group systems. This technique can be easily adapted to the genotyping of any polymorphic site.

Thus, according to a first aspect, the present invention concerns an in vitro method for detecting the allelic variants of one or more polymorphic sites in a nucleic acid, and more particularly for genotyping one or more single-nucleotide polymorphisms (SNPs).

A SNP is a variation at a single position in the genomic DNA between individuals of the same species (prokaryotic, eukaryotic or viral species). SNPs can be found within exons or introns or in intergenic regions. SNPs found in coding regions may or may not modify the amino acid sequence of the encoded protein. Those contained in non-coding regions can have effects on splicing or on transcription factors, for example. Although theoretically being able to have four alleles (A, T, C and G), most SNPs have only two. A SNP can be identified by the position of the nucleotide concerned by the polymorphism (for example, "125G>A" means that the nucleotide at position 125 of a given genomic sequence can be G or A), by the position of the amino acid residue concerned (for example, "Gly42Asp" means that the amino acid at position 42 of a given protein sequence can be glycine or aspartic acid), or by its identifier in a database listing the various SNPs, for instance the "NCBI SNP database" (see Worldwide Website: www.ncbi.nlm.nih.gov/SNP).

As used herein, the term "genotype a SNP" means to determine the allelic variants of a SNP which are present in the nucleic acid contained in a sample. This makes it possible, for example, to determine if an individual is homozygous (has two identical alleles) or heterozygous (has two different alleles) for a given SNP.

The nucleic acid contained in the sample to be genotyped can be DNA, RNA, a single- or double-stranded nucleic acid, or a mixture thereof. The nucleic acid is preferably a DNA, and particularly preferably a double-stranded DNA.

The nucleic acid can be of any origin, especially of human, animal, bacterial, viral or fungal origin. The nucleic acid is preferably of human or animal origin, and more particularly preferably, of human origin.

According to a preferred embodiment, the nucleic acid contained in the sample is genomic DNA or RNA, preferably genomic DNA.

The sample can be any biological sample containing nucleic acids, preferably any biological sample containing genomic DNA, such as, for example blood, plasma, serum, saliva, urine, seminal fluid samples or tissue or organ samples obtained from a subject (animal or human, preferably human). According to a particular embodiment, the sample is a total blood, plasma or serum sample obtained from an animal or human subject, preferably human.

The sample can optionally be subjected to a chemical, enzymatic, thermal and/or mechanical treatment before use. In particular, when the sample is a total blood sample, said sample can be mixed with an anticoagulant, preferably selected from EDTA and sodium citrate. The use of heparin, known to inhibit amplification reactions, is preferably avoided.

The sample can be used immediately after being collected, after storage at 4° C. or −20° C.

The sample can also be obtained by partial or total purification of the genomic DNA or RNA from a biological sample by means of any technique well-known to those skilled in the art.

According to a preferred embodiment, the sample is a total blood, plasma or serum sample, preferably a total blood sample, and the step of gene amplification of the nucleic acid contained in the sample as described below, is carried out preferably with no preliminary step of partial or total purification of the nucleic acid.

The method according to the invention can be used for the genotyping of a single SNP or of several SNPs. According to a preferred embodiment, the method is used for simultaneously genotyping several SNPs, preferably from 2 to 20, 15 or 10 SNPs, and particularly preferably from 2 to 5 SNPs.

The SNPs to be genotyped can be any SNP of interest. The SNPs can in particular be human, animal, plant, bacterial, fungal or viral SNPs. Preferably, the SNPs to be genotyped are human or animal SNPs. The SNPs can be, for example, SNPs associated with a disease, a predisposition to a disease, a therapeutic response, SNPs of interest for identifying individuals, notably in forensic medicine, or SNPs for the typing of blood group antigens.

According to a preferred embodiment, the SNPs to be genotyped are associated with one or more blood group systems. By way of example, said SNPs include, but are not limited to, SNP rs1058396 (NCBI SNP database) responsible for the polymorphism JK*1/JK*2; SNP rs12075 (NCBI SNP database) responsible for the polymorphism FY*1/FY*2; SNP rs2814778 (NCBI SNP database) responsible for the polymorphism FY*wt/FY*Fy; and SNP 143T>C in the gene encoding glycophorin B (GYPB) (GeneID: 2994) responsible for the polymorphism MNS*3/MNS*4.

The method according to the invention comprises a step of gene amplification of the nucleic acid contained in the sample followed by analysis of the amplification products using a lateral-flow assay device.

Thus, the method according to the invention comprises
a) amplifying one or more regions of the nucleic acid containing the SNP(s) to be genotyped, the amplification products comprising a label capable of directly or indirectly generating a detectable signal, and b) analysing the amplification products obtained in step (a) using a lateral-flow assay device comprising a reaction zone comprising one or more nucleotide probes immobilized on distinct sites, each probe having a sequence complementary to an allelic variant of a SNP to be genotyped, the detection of a signal at the probe immobilization site indicating that the nucleic acid comprises the specific allelic variant of the probe.

Unlike the methods described in the prior art, the gene amplification step a) of the method according to the invention is not carried out using primers specific for the allele to be detected. The primers are selected so as to flank the polymorphic site(s) to be genotyped. Preferably, none the primers overlap the polymorphic site to be analysed. A single amplification product is thus sufficient for genotyping the SNP(s) contained in the amplified region and for detecting the different allelic variants of the same SNP.

The technique used during this amplification step depends on the nature of the nucleic acid to be analysed and contained in the sample. The gene amplification can be carried out by any method known to those skilled in the art, notably by PCR, RT-PCR, rolling circle amplification (RCA), amplification by Qβ-replicase, ligase chain reaction (LCR), nucleic acid sequence-based amplification (NASBA), strand displacement amplification, loop-mediated isothermal amplification, hyperbranched rolling circle amplification (HRCA) or transcription-mediated amplification (TMA).

According to a particular embodiment, the nucleic acid contained in the sample is a DNA, preferably a genomic DNA, and the amplification is carried out by PCR, preferably by asymmetric PCR. The asymmetric PCR technique allows preferential amplification of one of the DNA strands in a matrix of double-stranded DNA. The PCR is carried out according to a standard protocol but with one of the primers in large excess relative to the other. During the first 20 to 25 cycles, the double-stranded DNA is generated, until the limiting primer is exhausted. Only single-stranded DNA is produced during the last cycles. The asymmetric PCR can in particular be a linear-after-the-exponential (LATE)-PCR (see WO 03/054233) or an improved LATE (imLATE)-PCR (Song et al., 2013).

Preferably, the asymmetric PCR is a LATE-PCR. LATE-PCR is a technique using a limiting primer with a melting point (Tm) at least 5° C. higher than that of the excess primer. This makes it possible to maintain satisfactory reaction efficiency when the concentration of limiting primer decreases (Pierce and Wangh, 2007). According to a particular embodiment, the amplification is carried out by LATE-PCR wherein the limiting primer(s) has/have a melting point (Tm) 6 to 8° C., preferably 6.7 to 7.7° C., higher than the excess primer(s).

When several regions of the nucleic acid must be amplified, the amplification is preferably carried out by means of multiplex PCR allowing simultaneous amplification, in the same reaction container, of several distinct regions by means of various primer pairs. Particularly preferably, the amplification is carried out by means of multiplex asymmetric PCR, notably multiplex LATE-PCR. Multiplex PCR techniques are well-known to those skilled in the art and are illustrated, for example, in the article by Paris et al., 2014, or in international patent application WO 03/054233.

The primers can be easily designed by those skilled in the art according to the region of the nucleic acid to be amplified and the technique used. As mentioned above, the primers flank the polymorphic sites to be analysed without overlapping them. The primers define the size of the amplification products. Preferably, the latter have a length of 25 to 500 nucleotides, preferably 50 to 250, 200, 180, 150 or 100 nucleotides.

In the method according to the invention, the amplification products (or amplicons) comprise a label capable of directly or indirectly generating a detectable signal. Labelling of the amplicons can be carried out during the amplification, notably by means of labelled primers or labelled nucleotides, or during a step subsequent to the amplification.

According to an embodiment, the amplicons are labelled during the amplification reaction. The amplicons can be 5'-labelled, 3'-labelled, or labelled at one or more internal sites. A great number of enzymatic or chemical techniques are known to those skilled in the art and commercially available for generating labelled amplicons.

According to a particular embodiment, the amplification products comprise a 5' labelling. Said labelling is preferably obtained during the amplification by using 5'-labelled primers. When the amplification is carried out by LATE-PCR, the labelled primer is the excess primer.

As used in the present document, the term "detectable signal" refers to a signal which can be perceived directly by the human eye or by means of a detection system. The nature of said signal varies according to the nature of the label used. The signal can in particular be a colored, luminescent, fluorescent, phosphorescent, radioactive or magnetic signal. Preferably, the signal is a colored signal.

The amplicons can be labelled with labels capable of directly generating a detectable signal, such as, for example, fluorescent compounds such as rhodamine, fluorescein, carboxytetramethylrhodamine (TAMRA), tetramethylrhodamine (TMR), sulphorhodamine 101, Texas Red, Rhodamine Red, Alexa, DyLight and phycocyanins, or radioactive elements such as $^{32}$P.

Alternatively, the amplicons can be labelled with labels capable of indirectly generating a detectable signal. As used herein, the term "indirectly" means that the label can generate a detectable signal only after interaction with another compound such as a substrate or a binding partner. The labels capable of indirectly generating a detectable signal can be, for example, the first member of a ligand/anti-ligand pair or an enzyme producing a detectable signal in the presence of a substrate. Examples of ligand/anti-ligand pairs considered in the method according to the invention include, but are not limited to, the following pairs: biotin/streptavidin, antigen/antibody notably biotin/anti-biotin antibody or digoxygenin/anti-digoxygenin antibody, molecule/receptor or sugar/lectin. The enzymes which can be used as labels can be horseradish peroxidase, alkaline phosphatase or β-galactosidase, for example.

According to a more particular embodiment, the amplification products are labelled, preferably 5'-labelled, with a biotin. Preferably, this labelling is obtained during the amplification by using a 5'-labelled primer.

After amplification, the amplicons thus obtained are analysed by means of a lateral-flow assay device for discriminating the allelic variants of the SNP(s) to be genotyped.

Lateral-flow assays have been thoroughly described in the literature and are commonly used for purposes of clinical, pharmaceutical, food or chemical analyses. They can be employed to detect the presence of many types of analytes, for instance antibodies, antigens, proteins, chemical molecules or, more recently, nucleic acids (e.g., Ang et al., 2012).

The methods described in the prior art wherein SNPs are detected using dipstick tests are based on PCR techniques using primers specific for the allele of interest. This means that the amplification reaction takes place only if the 3' region of the primer is perfectly complementary to the target sequence. Each allele-specific primer thus comprises a 5' label allowing it to hybridize with the probes immobilized on the dipstick. The length of the label is generally about 24 nucleotides (Litos et al., 2009; Sapountzi et al., 2015), which makes it easy to distinguish the different amplicons.

The lateral-flow assay device used in the method according to the invention has the feature of comprising a reaction zone comprising one or more nucleotide probes immobilized on distinct sites, each probe having a sequence complementary to an allelic variant of a SNP to be genotyped. This means that two probes specific for two alleles of the same SNP differ by only one nucleotide, that of the polymorphic site (not counting the possible additional nucleotides at the 3' or 5' ends of the specific primer sequences).

The term "lateral flow" refers to a liquid flow wherein all of the dissolved or dispersed compounds are transported by capillary action, preferably at equivalent speeds and a steady flow rate, laterally through a matrix. This term is the opposite of "preferential retention" wherein one or more compounds to be analysed or detected are retained or slowed via preferential interactions with the matrix. The term "lateral flow" is used herein for descriptive, non-limiting purposes. The device can in fact adopt any configuration which would make it possible to apply the principles of the present invention. The device can thus have a linear (dipstick test), radial, T-shaped, L-shaped, cross-shaped configuration, etc.

Typically, a lateral-flow assay device as used in the method according to the invention comprises a porous matrix comprising
 (i) a migration buffer application zone,
 (ii) an amplification product application zone positioned downstream of the migration buffer application zone, and
 (iii) a reaction zone positioned downstream of the amplification product application zone (and comprising one or more probes immobilized on distinct sites, each probe being specific for an allelic variant of a SNP to be genotyped).

The terms "downstream" and "upstream" are used herein in their common meaning. They specify the position of one element of the device in relation to another according to the direction of flow. If element A is downstream of element B, that means that the flow passes first by element B then by element A. Conversely, if element A is upstream of element B, that means that the flow passes first by element A then by element B.

The first probes of the reaction zone are positioned preferably from 1 to 10 cm, and more particularly preferably from 2 to 5 cm, from the amplification product application zone.

Optionally, the matrix can also comprise a reagent migration monitoring zone downstream of the reaction zone. This migration monitoring zone indicates to the user that at least a portion of the sample has passed through the matrix. The reagent immobilized on this zone must enable the generation of a signal when said reagent comes into contact with the migration buffer, optionally with an added label, substrate or binding partner capable of directly or indirectly generating a detectable signal.

The matrix can also comprise a labelling zone comprising a substrate or binding partner specific for the amplification product label, said substrate or binding partner being capable of directly or indirectly generating a detectable signal. The labelling zone is preferably positioned downstream of the migration buffer application zone and upstream of the amplification product application zone.

Each of the different zones of the porous matrix is in fluid communication with the adjacent zone(s).

Optionally, the matrix can be in fluid communication with an absorbent pad positioned downstream of the reaction zone or the monitoring zone when the latter is present.

According to a particular embodiment, the lateral-flow assay device as used in the method according to the invention comprises a porous matrix comprising
 (i) a migration buffer application zone,
 (ii) an amplification product application zone positioned downstream of the migration buffer application zone, and
 (iii) a reaction zone positioned downstream of the amplification product application zone,
 (iv) a migration monitoring zone downstream of the reaction zone, and
 (v) an absorbent pad positioned downstream of the monitoring zone.

Within the context of the lateral-flow assay, the amplification products are loaded onto a porous matrix through which they will migrate by capillary action to the reaction zone.

As used herein, the term "porous matrix" thus refers to any type of porous material capable of ensuring the flow and transfer of a fluid, preferably by force of capillary action. In particular, this term refers to any membrane suited to lateral-flow assays. By way of non-limiting examples, the porous matrix can be nitrocellulose, polyester, glass fiber, cellulose fiber, polyether sulphone (PES), a cellulose ester, etc. The various zones of the matrix can be made of the same material or of different materials. When the various zones of the matrix are made of different materials, the matrix is preferably formed by assembling the various elements. In order to ensure that the fluid communication is optimal between two adjacent elements, it is thus preferable to allow for a zone in which the two elements overlap by about 1 or 2 mm. By way of example, the amplification product application zone, the reaction zone and the migration monitoring zone can be made of nitrocellulose, the labelling zone made of glass fiber, and the absorbent pad and/or the migration buffer application zone made of cellulose fiber.

According to a particular embodiment, the porous matrix comprises a nitrocellulose membrane, preferably comprising the reaction zone. Particularly preferably, the nitrocellulose membrane comprises the reaction zone but also the amplification product application zone and/or the migration monitoring zone. Examples of nitrocellulose membranes include, but are not limited to, the following membranes: Millipore™ HF240, Millipore™ HF180, Millipore™ HF135, Millipore™ HF120, Millipore™ HF090, Millipore™ HF075, Sartorius™ CN140 and Sartorius™ CN150, FF120 HP membranes (GE), FF170HP membranes (GE), FF80HP membranes (GE), AE membranes (GE), Immunopore membranes (GE). Preferably, the nitrocellulose membrane has a capillary flow rate of 50 to 250 sec/4 cm, preferably 70 to 180 sec/4 cm, particularly preferably 100 to 170 sec/4 cm, and more particularly preferably 80 to 140 sec/4 cm.

The amplification product application zone is preferably made of nitrocellulose but can also be made of the same material as the migration buffer application zone, for example cellulose fiber. In the latter case, and in the embodiments where there is no labelling zone, the migration buffer application zone and the amplification product application zone can merge.

The labelling zone is made of a material capable of binding the substrate or binding partner specific for the amplification product label, for example glass fiber.

The absorbent pad and/or the migration buffer application zone are/is made of a material having a high absorption capacity, for example cellulose fiber.

The size of the matrix can be easily selected by those skilled in the art. According to certain preferred embodiments, said matrix is a strip having a length of 5 to 20 cm, preferably of 7 to 15 or 10 cm, and a width of 0.3 to 1 cm, preferably of 0.5 to 0.8 cm. Preferably, when the matrix is made up of various assembled elements, the latter are of the same width.

The porous matrix can be optionally attached to a solid support such as a plate or a cassette, generally made of plastic. The use of a solid support is particularly advantageous when the matrix consists of various assembled elements. The support can be, for example, a flexible plate on which the various elements of the porous matrix are assembled and attached.

According to an embodiment, the amplification products are subjected to thermal denaturation, typically for a few minutes at about 90-95° C., before being loaded onto the lateral-flow assay device, in order to increase the quantity of single-stranded nucleic acid.

According to another embodiment, the amplification products are analysed directly using the lateral-flow assay device with no preliminary purification or denaturation step. The amplification reaction products are thus loaded directly onto the amplification product application zone. This embodiment is all the more pertinent when the amplification is carried out by asymmetric PCR, and more particularly by LATE-PCR.

The reaction zone of the assay comprises one or more immobilized nucleotide probes which act as capture agents by specifically hybridizing with the amplification products. Each probe is immobilized on a distinct site and is specific for an allelic variant of a SNP to be genotyped.

The immobilized probes comprise a nucleotide sequence strictly complementary to the sequence of the allele of the polymorphic site of interest. These probes preferably have a length of 8 to 25 nucleotides, and more particularly preferably of 10 to 20 nucleotides (not counting optional spacers and poly(dT)) complementary to the target sequence.

According to an embodiment, 5 to 25 pmol, preferably 10 to 20 pmol, of each probe are loaded onto distinct sites in the reaction zone.

The nucleotide associated with the polymorphic site (i.e., the nucleotide that varies according to the allele to be detected) is preferably positioned in the middle, or substantially in the middle, of the nucleotide sequence specific for the target.

In addition to the sequence specific for the allele to be detected, the probes can also comprise one or more spacer groups at the 3' or 5' end, preferably at the 5' position. These groups can in particular be poly(dT) spacers or C3 to C12 spacers linked to one or more grafting groups, preferably C6 or C7. The grafting groups can in particular be amino, aldehyde, carboxyl groups, etc., preferably amino groups. According to a particular embodiment, the probes comprise a 5' poly(dT) spacer, preferably a poly(dT) spacer comprising from 5 to 20 dT, and particularly preferably 15 dT. According to another embodiment, the probes comprise a 5' C3 to C12 spacer, preferably, a C6 or C7 spacer linked to a grafting group, preferably an amino group, at the 5' end of the probe. According to a preferred embodiment, the probes comprise both a C3 to C12 spacer, preferably a C6 or C7 spacer, and a poly(dT) spacer, preferably comprising 5 to 20 dT, and particularly preferably 15 dT.

The various probes immobilized on the reaction zone are designed so as to have similar melting points (Tm). Preferably, the Tm of the various probes immobilized on the matrix vary by less than 8° C., and more particularly preferably by less than 6, 5, 4, 3 or 2° C.

The probes can be immobilized on the porous matrix according to techniques well-known to those skilled in the art. In particular, the probes can be immobilized on the matrix by covalent bond, adsorption or any other suitable method. Preferably, the probes are immobilized by adsorption.

The progression of the lateral-flow assay depends on the nature of the label used to mark the amplification products, i.e., a label capable of directly or indirectly generating a detectable signal.

If the amplification products are labelled with a label capable of indirectly generating a detectable signal, this means that the label can generate a detectable signal only after interaction with another compound such as a substrate or a binding partner.

In this case, two embodiments can be envisaged:

(i) the migration buffer comprises the substrate or binding partner capable of interacting with the label in order to directly or indirectly generate a detectable signal, or (ii) the lateral-flow assay device comprises a labelling zone comprising a substrate or binding partner specific for the amplification product label, said substrate or binding partner being capable of directly or indirectly generating a detectable signal. The labelling zone is preferably positioned downstream of the migration buffer application zone and upstream of the amplification product application zone.

According to a particular embodiment, the amplification product label is the first member of a ligand/anti-ligand pair. In this case, the migration buffer or the labelling zone comprises the second member of said pair, optionally conjugated to a detectable label. Examples of detectable labels include, but are not limited to, colloidal metals such as gold or silver; non-colloidal metals such as selenium, tellurium or sulphur particles; latex; visible, fluorescent, luminescent or chemiluminescent dyes; magnetic particles; radioactive elements; or enzymes. Preferably, the detectable label is a colored particle, for example a colloidal metal particle, particularly preferably a gold particle.

According to a preferred embodiment, the amplification product label is biotin and the migration buffer or the labelling zone comprises an anti-biotin antibody coupled to a detectable label, preferably coupled to a gold particle. In this embodiment, the migration monitoring zone can comprise a biotinylated molecule, for example biotinylated bovine serum albumin, loaded onto the matrix which will be revealed by the anti-biotin antibody coupled to a detectable label.

If the amplification products are labelled with a label capable of directly generating a detectable signal, this means that no substrate or binding partner is required to generate a detectable signal. Application of the migration buffer is sufficient to cause the amplification products to migrate towards the reaction zone and to generate a signal coming from the hybridization of the amplification products with the immobilized probes.

After loading the amplification products on the device, the migration buffer is applied to the device by immersing the application zone or by loading the buffer directly onto the application zone. Depending on the embodiment, the migration buffer comprises or does not comprise a substrate or binding partner for the amplification product label.

Optionally, the method can comprise an additional step consisting in "wetting" the porous matrix with the migration buffer before loading the amplification products. This "wetting" step can be done by immersing the buffer application zone or by loading the buffer directly onto the application zone. During this step, the matrix is preferably placed at the incubation temperature that will be used for hybridizing the probes with the amplification products.

The migration buffer preferably stabilizes the single-stranded structures during the migration, in order to obtain a homogeneous migration through the wetted membrane, to provide good particle mobility during the migration in order to avoid aggregation phenomena and to provide sufficient stringency to allow specific probe/target hybridization.

The migration buffer comprises, preferably, a buffer system for maintaining a neutral pH such as SSC, one or more surfactants such as SDS or TWEEN 20, and/or one or more denaturing agents, such as urea or formamide, which destabilize hydrogen bonds. According to an embodiment, the migration buffer comprises SSC, SDS, preferably 0.2 to 1%, TWEEN 20, preferably 5 to 20%, and formamide, preferably 2 to 10%. According to a particular embodiment, the migration buffer formulation is as follows: 1×SSC, 0.5% SDS, 10% TWEEN 20 and 5% formamide.

The assay device is then incubated until the signals generated directly or indirectly by the amplification product label are detected in the reaction zone and/or a signal is detected in the migration monitoring zone, when the latter is present.

The incubation temperature during this step depends essentially on the Tm of the immobilized probes. Preferably, the incubation temperature is selected so that no probe has a Tm which differs from the incubation temperature by more than 8° C., preferably by more than 7 or 6° C., and particularly preferably by more than 5° C.

Optionally, the method can further comprise, after incubation and before the reading of the results, a washing step. Said washing, intended to decrease the background noise, can be carried out by adding a volume of migration buffer on the buffer application zone, by immersion or direct deposit.

The results are read by detecting the signals generated by the immobilized probes. Depending on the nature of the signals, the detection is achieved by simple visual inspection or by means of a detection system. Preferably, the generated signal is a colored signal visible to the naked eye and the detection is achieved by simple visual inspection.

The results are then interpreted, the detection of a signal from the probe immobilization site indicating that the nucleic acid contained in the sample comprises the allelic variant complementary to the probe.

When the device comprises a migration monitoring zone, the results are considered valid when a signal is also detected in said zone.

According to a second aspect, the present invention also concerns a lateral-flow assay device as described above, and comprising
a porous matrix, optionally attached to a solid support, said matrix comprising
  (i) a migration buffer application zone,
  (ii) an amplification product application zone positioned downstream of the migration buffer application zone, and
  (iii) a reaction zone, preferably made of nitrocellulose, positioned downstream of the amplification product application zone and comprising one or more probes immobilized on distinct sites, each probe having a sequence complementary to an allelic variant of a SNP of interest.

The embodiments relating to the device and described above within the context of the first aspect of the present invention are also envisaged in this aspect.

According to a particular embodiment, the reaction zone comprises at least two probes specific for two different variants of the same SNP, or at least two probes specific for two different SNPs.

Optionally, the matrix can also comprise a reagent migration monitoring zone downstream of the reaction zone and/or a labelling zone downstream of the buffer application zone and upstream of the amplification product application zone.

Each of the different zones of the porous matrix is in fluid communication with the adjacent zone(s).

Optionally, the matrix can be in fluid communication with an absorbent pad positioned downstream of the reaction zone or the monitoring zone when the latter is present.

According to an embodiment, the device comprises a porous matrix, optionally attached to a solid support, said matrix comprising
  a migration buffer application zone made of cellulose fiber,
  an amplification product application zone made of nitrocellulose or of cellulose fiber, preferably made of nitrocellulose and
  a reaction zone made of nitrocellulose,
and optionally,
  a monitoring zone made of nitrocellulose, and/or
  an absorbent pad made of cellulose fiber, and/or
  a labelling zone made of glass fiber.

According to a particular embodiment, the device comprises a porous matrix, optionally attached to a solid support, said matrix comprising
  a migration buffer application zone made of cellulose fiber,
  an amplification product application zone, a reaction zone and a monitoring zone made of nitrocellulose,
  an absorbent pad made of cellulose fiber, and
  optionally, a labelling zone made of glass fiber.

According to another particular embodiment, the device comprises a porous matrix, optionally attached to a solid support, said matrix comprising
  a migration buffer application zone made of cellulose fiber,
  an amplification product application zone made of cellulose fiber,
  a reaction zone and a monitoring zone made of nitrocellulose,
  an absorbent pad made of cellulose fiber, and
  optionally, a labelling zone made of glass fiber.

According to a particular embodiment, the immobilized probe(s) is/are specific for one or more blood group antigen systems, preferably for one or more systems selected from the Duffy, MNS and Kidd systems. In particular, the probe(s) can be selected from the group consisting of the probes having the sequences of SEQ ID NO: 9 to 20.

In another aspect, the present invention also concerns a kit comprising a lateral-flow assay device according to the invention, and at least one primer pair for amplifying a genomic region containing one or more SNPs.

Preferably, the kit comprises one or more primer pairs for amplifying one or more genomic regions containing one or more SNPs associated with blood group antigen systems such as Duffy, MNS and Kidd. According to a particular embodiment, the kit comprises one or more primers selected from the group consisting of SEQ ID NO: 1 to 8. Preferably, the kit comprises one or more of the primer pairs (1) SEQ ID NO: 1 and 2, (2) SEQ ID NO: 3 and 4, (3) SEQ ID NO: 5 and 6, and (4) SEQ ID NO: 7 and 8.

The kit can also comprise a migration buffer, the amplification reagents, notably the reagents necessary for amplifying the targets by LATE-PCR, such as dNTPs, a polymerase or a buffer, and/or an instruction leaflet.

According to another aspect, the present invention concerns the use of a lateral-flow assay device according to the invention or a kit according to the invention for genotyping one or more SNPs according to the method of the invention.

The present invention also concerns the use of a lateral-flow assay device according to the invention or a kit according to the invention for typing an individual's blood group antigens from a sample, preferably a blood, plasma or serum sample. The typing can in particular concern one or more of the Duffy, MNS and Kidd systems.

sively genotyped using a blood group genotyping technique described previously (Paris et al., 2014).

Design of LATE-PCR Primers

The primers were designed to be used at non-stoichiometric concentrations and on the basis of an adjustment of the Tm values as a function of their working concentration, to meet the constraint (Tm limiting primer–Tm excess primer)≥5° C., enabling the generation of single-stranded products with high efficiency (Pierce et al., 2005; Sanchez et al., 2004). The primers were labelled at the 5' position with a biotin group to allow the detection of the hybridized targets via the appearance of colored spots on the nitrocellulose membrane, by the use of gold nanoparticles functionalized with an anti-biotin antibody. The primer sequences are described in Table 1.

TABLE 1

Primer sequences used for amplifying blood group systems by LATE-PCR.

| System | Allele | Primer type | Sequences | Conc. (µM) | Tm (° C.) |
|---|---|---|---|---|---|
| JK | JK*01/ JK*02 | Excess primer | 5'-Biotin-CAGTCTTTCAGCCCCATTTGAG-3' (SEQ ID NO: 1) | 1 | 56.1 |
| | | Limiting primer | 5'-GGTGAGCGCCATGAACATTCCTCCC-3' (SEQ ID NO: 2) | 0.1 | 63.8 |
| MNS | GYPB*03 (MNS*03)/ GYPB*04 (MNS*04) | Excess primer | 5'-Biotin-ACCTGGTACAGTGAAACGATG-3' (SEQ ID NO: 3) | 1 | 54.7 |
| | | Limiting primer | 5'-AGG AAA CCC GCA GAA CAG TTT GAT TCC-3 (SEQ ID NO: 4) | 0.1 | 60.2 |
| FY | FY*01/FY*02 | Excess primer | 5'-Biotin-ATGATTCCTTCCCAGATGGAGAC-3' (SEQ ID NO: 5) | 1 | 56.3 |
| | | Limiting primer | 5'-TGCAGAGTCATCCAGCAGGTTACAGGAGT-3' (SEQ ID NO: 6) | 0.1 | 64 |
| | FY*02M.02 (FY*Fy) | Excess primer | 5'-Biotin-CCCTCATTAGTCCTTGGCTCTT-3' (SEQ ID NO: 7) | 1 | 56.4 |
| | | Limiting primer | 5'-CTCACCCTGTGCAGACAGTTCCCC-3' (SEQ ID NO: 8) | 0.1 | 63.5 |

All references cited in this description are incorporated by reference in the present application. Other features and advantages of the invention will become more readily apparent from reading the following examples given on a purely illustrative and non-limiting basis.

EXAMPLES

Example 1

Materials and Methods

Sodium chloride, sodium citrate, methanol, sucrose, sodium dodecyl sulphate (SDS), TWEEN 20, formamide, and biotinylated bovine serum albumin were purchased from Sigma-Aldrich. Gold particles conjugated to an anti-biotin antibody (40 nm, 9×10$^{10}$ particles/mL) were purchased from BBI Solutions (England). Oligonucleotides, primers and Probes were Synthesized by Eurogentec (Belgium).

Total blood samples, phenotyping and genotyping technique

Total blood samples were collected, on anticoagulant (EDTA), by the Etablissement Français du Sang Rhône-Alpes and were extensively phenotyped using standard serological techniques in the Blood Donation Qualification Laboratory (Metz-Tessy, France). The samples were exten- LATE-PCR Amplification Conditions Genomic DNA extraction was carried out from 400 µL of total blood on a MagNA Pure Compact System (Roche Diagnostics, Switzerland), using the MagNA Pure Compact Isolation Kit I (Roche Diagnostics, Switzerland). After extraction, the DNA was eluted in 100 µL of buffer solution and quantified on a NanoVue spectrophotometer (GE Healthcare, USA).

Monoplex LATE-PCR Amplification Conditions.

The master mix contained 1 µL of genomic DNA, 1× buffer (Eurogentec, Belgium), MgCl$_2$ (1.5 mM), dNTPs (0.2 mM), HOTGOLDSTAR Diamond Taq DNA polymerase (5 units per µL), and the specific primers.

Monoplex PCR was carried out on a TProfessional thermocycler (Biometra, Germany), starting with a step of enzyme activation at 95° C. for 3 minutes, followed by 35 cycles at 95° C. for 30 seconds, 55.5° C. for 30 seconds, and 72° C. for 30 seconds. The amplification products were monitored by UV illumination of a 2% agarose gel loaded with GELRED (Biotum, USA).

Multiplex LATE-PCR amplification conditions. The genomic DNA was used to simultaneously amplify, and in a single PCR microtube, 86 to 133 bp genomic fragments. Conditions for unconventional asymmetric PCR, LATE-PCR, were applied for the amplification of alleles JK*01/ JK*02, FY*wt/FY*02M.02 (FY*Fy) and GYPB*03

(MNS*03)/GYPB*04 (MNS*04) (Table 1). The master mix contained 2.5 μL of genomic DNA, 1× KAPA2G buffer, $MgCl_2$ (1.5 mM), bovine serum albumin (BSA, 0.5 mg/mL), dNTPs (0.2 mM), KAPA2G Fast HotStart DNA polymerase (5 units per μL), and the specific primers.

Multiplex PCR was carried out on a LIGHTCYCLER 2.0 instrument (Roche Diagnostics, Germany), with high temperature ramp rates. A first step of enzyme activation at 95° C. for 30 seconds was followed by 45 cycles at 95° C. for 5 seconds, 55° C. for 10 seconds, and 72° C. for 10 seconds. The amplification products were monitored by UV illumination of a 2% agarose gel loaded with GELRED (Biotum, USA).

Preparation of Nitrocellulose Membranes

HF135 nitrocellulose membranes (Millipore, USA) were purchased from Millipore (USA). The probes were specially designed to detect the alleles of the three blood group systems (Table 2). Probes were designed with a $dT_{15}$ poly (dT) spacer at the 5' position, between the amino linker and the specific sequence, in order to increase hybridization efficiency. The dipsticks were assembled with a nitrocellulose membrane (80 mm×5 mm) and an absorbent pad. The membrane and the absorbent pad were cut using a guillotine cutter.

A biotinylated-BSA solution at a concentration of 5 mg·mL$^{-1}$ was immobilized on the upper portion of the dipstick to form a control zone (CT) during the assay.

The probes were manually loaded onto the membrane using a probe solution at a concentration of 50 μM·L$^{-1}$ in loading buffer (6×SSC, 0.1% SDS, 2% methanol, 2% sucrose). After loading, the membranes were dried at 80° C. for 45 minutes.

Visual Detection of Blood Group Genotype on a Membrane

With neither a purification step nor a denaturation step, the PCR products were applied directly to the lower portion of the membrane (between 1 and 1.5 cm above the bottom of the membrane), which was then immersed in a well of a 96-well microplate containing 10 μL of a solution of conjugated gold nanoparticles diluted twice in the migration buffer (1×SSC, 0.5% SDS, 10% TWEEN 20, 5% formamide). After migration of the nanoparticles, the membrane was immersed in a first 50-mL conical tube (Greiner Bio-One, Germany) containing 100 μL of migration buffer and incubated at 53° C. After 5 minutes of migration, the membrane was immersed in a fresh solution of gold nanoparticles diluted twice in the migration buffer.

After migration of the nanoparticles, the membrane was again immersed in a 50-mL conical tube (Greiner Bio-One, Germany) and incubated at 53° C. Visual detection of the blood group genotyping was complete in 30 minutes.

Results

The inventors have developed a blood group genotyping assay by migration of amplified targets on a nitrocellulose membrane, in a monoplex format.

The targets of interest for the two blood group systems, JK (JK*1/JK*2) and FY (FY*1/FY*2), were amplified by monoplex LATE-PCR. Inspection of the amplification products on 2% agarose gel showed the presence of bands of the expected sizes (JK*1/JK*2: 100 bp, FY*1/FY*2: 86 bp) (FIG. 7).

Six samples having different profiles (FIGS. 2 and 3), the phenotype and genotype of which had been determined beforehand by reference techniques (phenotype determined by serology, genotype by the use of DNA microarrays (Paris et al., 2014)), were amplified using the LATE-PCR protocol. The PCR products were applied to a nitrocellulose membrane (HF135, Millipore) onto which the probes specific for the alleles of interest had been loaded.

Figure 1B:
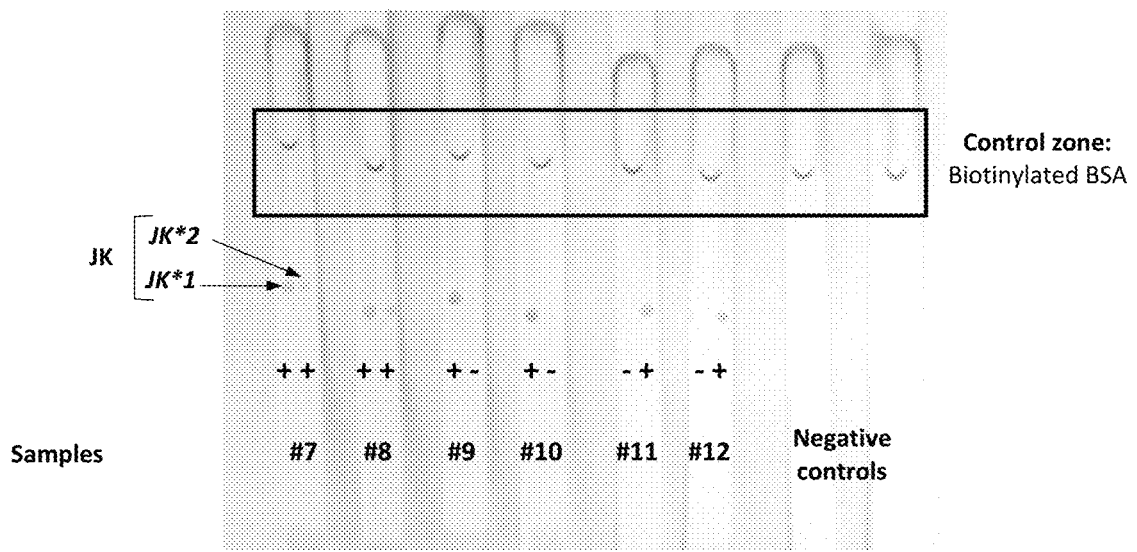

The appearance of a colored zone, after their migration by lateral flow, showed the possibility of visually detecting the presence and/or absence of the amplified alleles, of determining a blood group genotype in agreement with the results obtained by the reference techniques, and of discriminating the different genotypes for the JK and FY systems (FIGS. 1A and 1B). The appearance of coloring on the dipstick's control zone (biotinylated BSA) validated the proper func-

TABLE 2

Probe sequences used during multiplex blood group genotyping.

| System | Allele | Sequences | $T_m$ (° C.) |
|---|---|---|---|
| JK | JK*01 | 5'-C$_6$NH$_2$-(dT)$_{15}$AGTAGATGTCCTCAAATGG-3' (SEQ ID NO: 9) | 48.7 |
|  | JK*02 | 5'-C$_6$NH$_2$-(dT)$_{15}$AAGTAGATGTTCTCAAATGGG-3' (SEQ ID NO: 10) | 50 |
| FY | FY*01 | 5'-C$_6$NH$_2$-(dT)$_{15}$AGGTTGGCACCATAGTCTC-3' (SEQ ID NO: 11) | 54.2 |
|  | FY*02 | 5'-C$_6$NH$_2$-(dT)$_{15}$AGGTTGGCATCATAGTCTC-3' (SEQ ID NO: 12) | 51.5 |
|  | FY*wt | 5'-C$_6$NH$_2$-(dT)$_{15}$GCTTCCAAGATAAGAGCCA-3' (SEQ ID NO: 13) | 52 |
|  | FY*02M.02 (FY*Fy) | 5'-C$_6$NH$_2$-(dT)$_{15}$GCTTCCAAGGTAAGAGCCA-3' (SEQ ID NO: 14) | 54.7 |
| MNS | GYPB*03 (MNS*03) | 5'-C$_6$NH$_2$-(dT)$_{15}$AGGAGAAATGGGACAACTTG-3' (SEQ ID NO: 15) | 52.4 |
|  | GYPB*04 (MNS*04) | 5'-C$_6$NH$_2$-(dT)$_{15}$ATAGGAGAAACGGGACAACTT-3' (SEQ ID NO: 16) | 53.5 |

Polymorphisms (SNPs) for each probe are indicated by the nucleotide in bold and underlined.

tioning of the detection particles as well as the satisfactory migration thereof through the membrane during the assay.

The inventors have also developed a blood group genotyping assay by migration of amplified targets on a nitrocellulose membrane, in a multiplex format integrating new systems of interest (MNS: MNS*3/MNS*4, FY: FY*wt/FY*Fy).

Figure 1C:
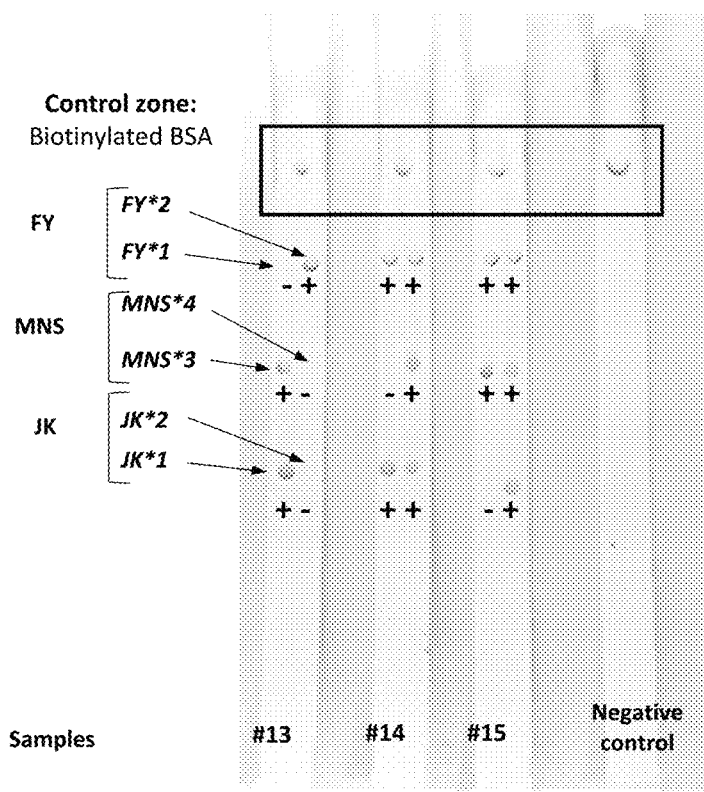
Figure 1D:
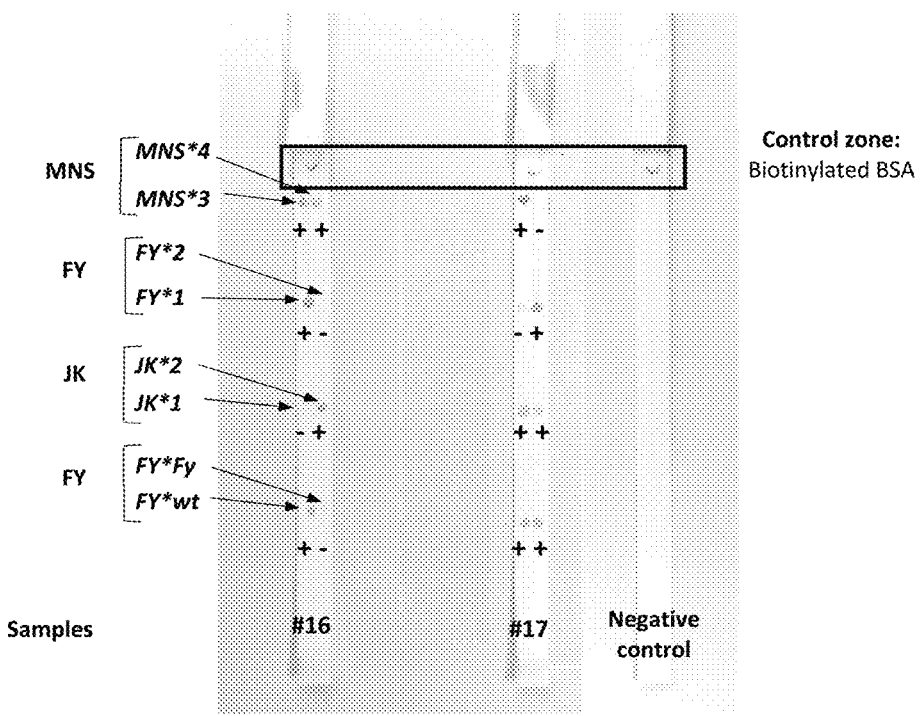

New probes specific for each allele were designed and then loaded onto the membrane in order to carry out the genotyping assay. Five genomic DNA samples having different profiles (FIG. 4) were amplified by multiplex LATE-PCR. Their migration on a lateral-flow system led to the appearance of colored zones (FIGS. 1C and 1D) and allowed the determination of the genotype for each sample. The results obtained were in agreement between the phenotypes predicted from the genotype and the reference techniques and prove the possibility of simultaneously determining a blood group genotype for the six antigens of interest (FIG. 1D) in a multiplex format and of predicting the extended phenotype.

Example 2

Materials and Methods

New probes were designed to allow the determination of a blood group genotype at lower migration temperatures than that presented in example 1. The sequences are presented in table 3. The dipsticks were assembled with an HF090 nitrocellulose membrane (80 mm×5 mm) and an absorbent pad. The membrane and the absorbent pad were cut using a guillotine cutter.

A biotinylated-BSA solution at a concentration of 5 mg·mL$^{-1}$ was immobilized on the upper portion of the dipstick to form a control zone (CT) during the assay.

The probes were manually loaded onto the membrane using a probe solution at a concentration of 50 µM·L$^{-1}$ in loading buffer (6×SSC, 0.1% SDS, 2% methanol, 2% sucrose). After loading, the membranes were dried at 80° C. for 40-45 minutes.

TABLE 3

Probe sequences used during multiplex blood group genotyping of the JK and FY systems.

| System | Allele | Sequence | $T_m$ (° C.) |
|---|---|---|---|
| JK | JK*01 | 5'-C$_6$NH$_2$-(dT)$_{15}$AGATGTCCTCAA-3' (SEQ ID NO: 17) | 34.3 |
|  | JK*02 | 5'-C$_6$NH$_2$-(dT)$_{15}$TAGATGTTCTCAAT-3' (SEQ ID NO: 18) | 33.8 |
| FY | FY*01 | 5'-C$_6$NH$_2$-(dT)$_{15}$TGGCACCATAG-3' (SEQ ID NO: 19) | 35.7 |
|  | FY*02 | 5'-C$_6$NH$_2$-(dT)$_{15}$TGGCATCATAGT-3' (SEQ ID NO: 20) | 35.0 |

Polymorphisms (SNPs) for each probe are indicated by the nucleotide in bold and underlined.

The PCR products were applied directly to the lower portion of the membrane which was then immersed in a well of a 96-well microplate containing 10 µL of a solution of conjugated gold nanoparticles diluted twice in the migration buffer (1×SSC, 0.5% SDS, 10% TWEEN 20, 5% formamide). After migration of the nanoparticles, the membrane was immersed in a 50-mL conical tube (Greiner Bio-One, Germany) containing 100 µL of migration buffer and incubated at 30° C. Visual detection of the blood group genotyping was complete in less than 30 minutes.

Results

The method for blood group genotyping on a lateral-flow system described in example 1 was adapted to allow that assay to be carried out at a temperature of 30° C.

The targets of interest for the two blood group systems, JK (JK*1/JK*2) and FY (FY*1/FY*2), were amplified by duplex LATE-PCR. By comparison with the method described in example 1, the size of the probes was reduced and the nitrocellulose membrane was replaced with a membrane having a higher capillary flow rate (HF090 nitrocellulose membrane).

Three genomic DNA samples having different profiles were amplified by duplex LATE-PCR and applied to the nitrocellulose membrane onto which the probes specific for the alleles concerned had been loaded. The appearance of colored spots on the membrane's reaction zone (FIG. 5) made it possible to simultaneously determine the genotype for the JK and FY systems and to predict the phenotypes. The results obtained were in agreement with those determined by the other reference techniques.

Example 3

The inventors have also shown that the method for blood group genotyping according to the invention could be implemented directly from a total blood sample.

To that end, the targets of interest for the four blood group systems, JK (JK*1/JK*2), FY (FY*1/FY*2), MNS (MNS*3/MNS*4) and FY (FY*wt/FY*Fy), were amplified by multiplex LATE-PCR according to the protocol detailed in example 1, using 2.5 µL of total blood instead of genomic DNA.

Four samples having different profiles the phenotype and genotype of which had been determined beforehand by reference techniques (phenotype determined by serology, genotype by the use of DNA microarrays (Paris et al., 2014)) were amplified using the LATE-PCR protocol. The PCR products were applied to a nitrocellulose membrane (HF135, Millipore) to which the probes specific for the alleles of interest had been loaded (see example 1).

The appearance of a colored zone, after their migration by lateral flow, made it possible to determine a blood group genotype in agreement with the results obtained by the reference techniques (FIG. 8).

REFERENCES

Ang et al. Biosensors and Bioelectronics 38 (2012) 151-156

Paris, S., et al., J Mol Diagn, 2014. 16(3): p. 335-42

Pierce, K. E., et al., Proceedings of the National Academy of Sciences of the United States of America, 2005. 102(24): p. 8609-8614.

Pierce K E and Wangh L J (2007). Methods Mol Med. Methods in Molecular Medicine 132: 65-85

Sanchez, J. A., et al., Proceedings of the National Academy of Sciences of the United States of America, 2004. 101(7): p. 1933-1938.

Song et al., Analyst, 2013, 138, 4991

The invention claimed is:

1. An in vitro method for genotyping one or more single-nucleotide polymorphisms (SNPs) in a nucleic acid sample, said method comprising:
   a) amplifying one or more regions of the nucleic acid containing the SNP(s) to be genotyped, the amplification products comprising a label capable of directly or indirectly generating a detectable signal, the amplification products being labelled during amplification reaction by means of labelled primers or labelled nucleotides and
   b) analyzing the amplification products obtained in step (a) using a lateral-flow assay device comprising a porous matrix comprising a reaction zone comprising one or more nucleotide capture probes immobilized on distinct sites of the reaction zone and being able to specifically hybridize with the amplification products, each capture probe having a sequence complementary to an allelic variant of a single SNP to be genotyped,
   c) the detection of the signal at the capture probe immobilization site indicating that the nucleic acid comprises the allelic variant specific of the probe.

2. The method according to claim 1, wherein the amplification is carried out by asymmetric PCR.

3. The method according to claim 1, wherein the simultaneous amplification of several regions of the nucleic acid is carried out by multiplex PCR.

4. The method according to claim 1, wherein the amplification products are 5'-labelled.

5. The method according to claim 1, wherein the amplification products are labelled with a colored compound, luminescent compound, fluorescent compound, phosphorescent compound, radioactive compound, an enzyme or a member of a ligand/anti-ligand pair.

6. The method according to claim 1, wherein the porous matrix comprising:
(i) a migration buffer application zone,
(ii) an amplification product application zone positioned downstream of the migration buffer application zone, and
(iii) the reaction zone positioned downstream of the amplification product application zone, and
(iv) optionally, a reagent migration monitoring zone downstream of the reaction zone, and/or
(v) optionally, a labelling zone comprising a substrate or binding partner specific for the amplification product label capable of directly or indirectly generating a detectable signal, positioned downstream of the migration buffer application zone and upstream of the amplification product application zone, and/or
(vi) optionally, an absorbent pad positioned downstream of the reaction zone or the monitoring zone when the latter is present,
the various zones of the porous matrix being in fluid communication with the adjacent zone(s) and the absorbent pad being in fluid communication with the porous matrix.

7. The method according to claim 1, wherein the amplification products are analyzed directly using the lateral-flow assay device with no preliminary purification or denaturation step.

8. The method according to claim 6, wherein the analysis comprises:
i) loading the amplification products obtained in step (a) onto the lateral-flow assay device,
ii) applying a migration buffer on said device,
iii) incubating the device until the signals generated directly or indirectly by the amplification product label are detected in the reaction zone and/or a signal is detected in the migration monitoring zone, when the latter is present, and
iv) reading and interpreting the results.

9. The method according to claim 6, wherein the matrix is selected from the group consisting of nitrocellulose, polyester, glass fiber, cellulose fiber, polyether sulphone (PES) and cellulose ester, and combinations thereof.

10. The method according to claim 9, wherein the matrix comprises a nitrocellulose membrane.

11. The method according to claim 10, wherein the nitrocellulose membrane comprises the reaction zone of the matrix.

12. The method according to claim 11, wherein the nitrocellulose membrane further comprises the amplification product application zone and/or the monitoring zone of the matrix.

13. The method according to claim 6, wherein the migration buffer application zone of the matrix and/or the absorbent pad are made of cellulose fiber.

14. The method according to claim 6, wherein the labelling zone of the matrix is made of glass fiber.

15. The method according to claim 8, wherein the migration buffer comprises a buffer system for maintaining a neutral pH, one or more surfactants and/or one or more denaturing agents that destabilize hydrogen bonds.

16. The method according to claim 1, wherein the nucleic acid to be genotyped and contained in the sample is genomic DNA.

17. The method according to claim 1, wherein the nucleic acid sample is a blood, serum or plasma sample.

18. The method according to claim 17, wherein the step of amplifying one or more regions of the nucleic acid containing the SNP(s) to be genotyped is carried out on the blood, serum or plasma sample, with no preliminary step of partial or total purification of the nucleic acid.

19. The method according to claim 6, wherein the amplification product label is biotin, and the migration buffer or the labelling zone comprises an anti-biotin antibody coupled to a detectable label.

* * * * *

SEQUENCE LISTING

<160> NUMBER OF SEQ ID NOS: 20

<210> SEQ ID NO 1
<211> LENGTH: 22
<212> TYPE: DNA
<213> ORGANISM: Artificial Sequence
<220> FEATURE:
<223> OTHER INFORMATION: Excess primer for LATE-PCR amplification of the
      SNP specific of JK system
<220> FEATURE:
<221> NAME/KEY: misc_feature
<223> OTHER INFORMATION: 5'biotinylated primer

<400> SEQUENCE: 1
cagtctttca gccccatttg ag                                              22

<210> SEQ ID NO 2
<211> LENGTH: 25
<212> TYPE: DNA
<213> ORGANISM: Artificial Sequence
<220> FEATURE:
<223> OTHER INFORMATION: Limiting primer for LATE-PCR amplification of
      the SNP specific of JK system

<400> SEQUENCE: 2
ggtgagcgcc atgaacattc ctccc                                           25

<210> SEQ ID NO 3
<211> LENGTH: 21
<212> TYPE: DNA
<213> ORGANISM: Artificial Sequence
<220> FEATURE:
<223> OTHER INFORMATION: Excess primer for LATE-PCR amplification of the
      SNP specific of MNS system
<220> FEATURE:
<221> NAME/KEY: misc_feature
<223> OTHER INFORMATION: 5'biotinylated primer

<400> SEQUENCE: 3
acctggtaca gtgaaacgat g                                               21

<210> SEQ ID NO 4
<211> LENGTH: 27
<212> TYPE: DNA
<213> ORGANISM: Artificial Sequence
<220> FEATURE:
<223> OTHER INFORMATION: Limiting primer for LATE-PCR amplification of
      the SNP specific of MNS system

<400> SEQUENCE: 4
aggaaacccg cagaacagtt tgattcc                                         27

<210> SEQ ID NO 5
<211> LENGTH: 23
<212> TYPE: DNA
<213> ORGANISM: Artificial Sequence
<220> FEATURE:
<223> OTHER INFORMATION: Excess primer for LATE-PCR amplification of the
      SNP specific of FY system
<220> FEATURE:
<221> NAME/KEY: misc_feature
<223> OTHER INFORMATION: 5'biotinylated primer

<400> SEQUENCE: 5
atgattcctt cccagatgga gac                                             23

<210> SEQ ID NO 6
<211> LENGTH: 29

```
<212> TYPE: DNA
<213> ORGANISM: Artificial Sequence
<220> FEATURE:
<223> OTHER INFORMATION: Limiting primer for LATE-PCR amplification of
      the SNP specific of FY system

<400> SEQUENCE: 6
tgcagagtca tccagcaggt tacaggagt                                        29

<210> SEQ ID NO 7
<211> LENGTH: 22
<212> TYPE: DNA
<213> ORGANISM: Artificial Sequence
<220> FEATURE:
<223> OTHER INFORMATION: Excess primer for LATE-PCR amplification of the
      SNP specific of FY (FY*Fy) system
<220> FEATURE:
<221> NAME/KEY: misc_feature
<223> OTHER INFORMATION: 5'biotinylated primer

<400> SEQUENCE: 7
ccctcattag tccttggctc tt                                               22

<210> SEQ ID NO 8
<211> LENGTH: 24
<212> TYPE: DNA
<213> ORGANISM: Artificial Sequence
<220> FEATURE:
<223> OTHER INFORMATION: Limiting primer for LATE-PCR amplification of
      the SNP specific of FY (FY*Fy) system

<400> SEQUENCE: 8
ctcaccctgt gcagacagtt cccc                                             24

<210> SEQ ID NO 9
<211> LENGTH: 19
<212> TYPE: DNA
<213> ORGANISM: Artificial Sequence
<220> FEATURE:
<223> OTHER INFORMATION: specific probe of the JK*01 allele
<220> FEATURE:
<221> NAME/KEY: misc_feature
<223> OTHER INFORMATION: 5' spacer group C6 NH2-(dT)15

<400> SEQUENCE: 9
agtagatgtc ctcaaatgg                                                   19

<210> SEQ ID NO 10
<211> LENGTH: 21
<212> TYPE: DNA
<213> ORGANISM: Artificial Sequence
<220> FEATURE:
<223> OTHER INFORMATION: specific probe of the JK*02 allele
<220> FEATURE:
<221> NAME/KEY: misc_feature
<223> OTHER INFORMATION: 5' spacer group C6 NH2-(dT)15

<400> SEQUENCE: 10
aagtagatgt tctcaaatgg g                                                21

<210> SEQ ID NO 11
<211> LENGTH: 19
<212> TYPE: DNA
<213> ORGANISM: Artificial Sequence
<220> FEATURE:
<223> OTHER INFORMATION: specific probe of the  FY*01 allele
<220> FEATURE:
<221> NAME/KEY: misc_feature
<223> OTHER INFORMATION: 5' spacer group C6 NH2-(dT)15
```

```
<400> SEQUENCE: 11
aggttggcac catagtctc                                                    19

<210> SEQ ID NO 12
<211> LENGTH: 19
<212> TYPE: DNA
<213> ORGANISM: Artificial Sequence
<220> FEATURE:
<223> OTHER INFORMATION: specific probe of the  FY*02 allele
<220> FEATURE:
<221> NAME/KEY: misc_feature
<223> OTHER INFORMATION: 5' spacer group C6 NH2-(dT)15

<400> SEQUENCE: 12
aggttggcat catagtctc                                                    19

<210> SEQ ID NO 13
<211> LENGTH: 19
<212> TYPE: DNA
<213> ORGANISM: Artificial Sequence
<220> FEATURE:
<223> OTHER INFORMATION: specific probe of the FY*wt allele
<220> FEATURE:
<221> NAME/KEY: misc_feature
<223> OTHER INFORMATION: 5' spacer group C6 NH2-(dT)15

<400> SEQUENCE: 13
gcttccaaga taagagcca                                                    19

<210> SEQ ID NO 14
<211> LENGTH: 19
<212> TYPE: DNA
<213> ORGANISM: Artificial Sequence
<220> FEATURE:
<223> OTHER INFORMATION: specific probe of the FY*02M.02 (FY*Fy) allele
<220> FEATURE:
<221> NAME/KEY: misc_feature
<223> OTHER INFORMATION: 5' spacer group C6 NH2-(dT)15

<400> SEQUENCE: 14
gcttccaagg taagagcca                                                    19

<210> SEQ ID NO 15
<211> LENGTH: 20
<212> TYPE: DNA
<213> ORGANISM: Artificial Sequence
<220> FEATURE:
<223> OTHER INFORMATION: specific probe of the MNS*03 allele
<220> FEATURE:
<221> NAME/KEY: misc_feature
<223> OTHER INFORMATION: 5' spacer group C6 NH2-(dT)15

<400> SEQUENCE: 15
aggagaaatg ggacaacttg                                                   20

<210> SEQ ID NO 16
<211> LENGTH: 21
<212> TYPE: DNA
<213> ORGANISM: Artificial Sequence
<220> FEATURE:
<223> OTHER INFORMATION: specific probe of the MNS*04 allele
<220> FEATURE:
<221> NAME/KEY: misc_feature
<223> OTHER INFORMATION: 5' spacer group C6 NH2-(dT)15

<400> SEQUENCE: 16
ataggagaaa cgggacaact t                                                 21
```

```
<210> SEQ ID NO 17
<211> LENGTH: 12
<212> TYPE: DNA
<213> ORGANISM: Artificial Sequence
<220> FEATURE:
<223> OTHER INFORMATION: specific probe of the JK*01 allele
<220> FEATURE:
<221> NAME/KEY: misc_feature
<223> OTHER INFORMATION: 5' spacer group C6 NH2-(dT)15

<400> SEQUENCE: 17
agatgtcctc aa                                                          12

<210> SEQ ID NO 18
<211> LENGTH: 14
<212> TYPE: DNA
<213> ORGANISM: Artificial Sequence
<220> FEATURE:
<223> OTHER INFORMATION: specific probe of the JK*02 allele
<220> FEATURE:
<221> NAME/KEY: misc_feature
<223> OTHER INFORMATION: 5'spacer group C6 NH2-(dT)15

<400> SEQUENCE: 18
tagatgttct caat                                                        14

<210> SEQ ID NO 19
<211> LENGTH: 11
<212> TYPE: DNA
<213> ORGANISM: Artificial Sequence
<220> FEATURE:
<223> OTHER INFORMATION: specific probe of the FY*01 allele
<220> FEATURE:
<221> NAME/KEY: misc_feature
<223> OTHER INFORMATION: 5' spacer group C6 NH2-(dT)15

<400> SEQUENCE: 19
tggcaccata g                                                           11

<210> SEQ ID NO 20
<211> LENGTH: 12
<212> TYPE: DNA
<213> ORGANISM: Artificial Sequence
<220> FEATURE:
<223> OTHER INFORMATION: specific probe of the FY*02 allele
<220> FEATURE:
<221> NAME/KEY: misc_feature
<223> OTHER INFORMATION: 5' spacer group C6 NH2-(dT)15

<400> SEQUENCE: 20
tggcatcata gt                                                          12
```